(12) United States Patent
Ledezma

(10) Patent No.: US 11,110,165 B2
(45) Date of Patent: Sep. 7, 2021

(54) THERAPEUTIC VACCINE FOR THE TREATMENT OF PAPILLOMAVIRUS LESIONS

(71) Applicant: Ricardo Rosales Ledezma, Cuernavaca (MX)

(72) Inventor: Ricardo Rosales Ledezma, Cuernavaca (MX)

(73) Assignee: Ricardo Rosales Ledezma, Cuernavaca (MX)

( * ) Notice: Subject to any disclaimer, the term of this patent is extended or adjusted under 35 U.S.C. 154(b) by 0 days.

(21) Appl. No.: 16/598,516

(22) Filed: Oct. 10, 2019

(65) Prior Publication Data

US 2021/0106675 A1 Apr. 15, 2021

(51) Int. Cl.
| | | |
|---|---|---|
| A61K 39/285 | (2006.01) | |
| C12N 7/04 | (2006.01) | |
| A61K 39/00 | (2006.01) | |

(52) U.S. Cl.
CPC ............. *A61K 39/285* (2013.01); *C12N 7/04* (2013.01); *A61K 2039/5254* (2013.01); *A61K 2039/585* (2013.01)

(58) Field of Classification Search
None
See application file for complete search history.

(56) References Cited

U.S. PATENT DOCUMENTS

| | | |
|---|---|---|
| 6,582,693 B2 | 6/2003 | Ledezma |
| 8,859,256 B2 | 10/2014 | Szalay et al. |
| 8,986,674 B2 | 3/2015 | Kim et al. |
| 10,105,436 B2 | 10/2018 | Szalay et al. |
| 2009/0169512 A1 | 7/2009 | Weltzin et al. |
| 2018/0326048 A1 | 11/2018 | Szalay et al. |

FOREIGN PATENT DOCUMENTS

WO 2019033030 A1 2/2019

OTHER PUBLICATIONS

Product Information Sheet for NR-2637, Genomic DNA from Vaccinia Virus, Lederle-Chorioallantoic, beiresources, Biodefense and Emerging Infections Research Resources Repository, 2006/2009, 1 page.
Davies, et al., "Antibody Profiling by Proteome Microarray Reveals the Immunogenicity of the Attenuated Smallpox Vaccine Modified Vacinia Virus Anakara is Comparable to That of Dryvax", Journal of Virology, vol. 82, No. 2, Jan. 2008, pp. 652-663.
Yakubitskiy, et al., "Attenuation of Vaccina Virus", Acta Naturae, vol. 7, No. 4(27), 2015, pp. 113-121.
Valdez, et al., "Human Tumor Growth is Inhibited by a Vaccinia Virus Carrying the E2 Gene of Bovine Papillomavirus", American Cancer Society, Apr. 1, 2000, vol. 88, No. 7, pp. 1650-1662.
Das, et al., "A Multiplex PCR/LDR Assay for the Simultaneous Identification of a Category A Infectious Pathogens: Agent of Viral Hemorragic Fever and Variola Virus", PLOS One,DOI:10.1371/journal.pone.0138484, Sep. 18, 2015, pp. 1-16.
Rosales, et al., "Regression of Human Papillomavirus Intraephithelial Lesions is Induced by MVA E2 Therapeutic Vaccine," Human Gene Therapy, vol. 25, Dec. 2014, pp. 1035-1049.
Jacobs, et al., "Vaccinia Virus Vaccines: Past, Present and Future", Antiviral Res. Oct. 2009; 84(1): 1-13, doi:0.1016/j.antiviral.2009.06.0006, pp. 1-28.
Zeh, et al., "First-in-man Study of Western Reserve Strain Oncolytic Vaccinia Virus: Safety, Systemic Spread, and Antitumor Activity", The American Society of Gene & Cell Therapy, www.moleculartherapy.org, vol. 23, No. 1, Jan. 2015, pp. 202-214.
Product Sheet, ATCC, Vaccinia Virus (ATCC VR-1354), American Type Culture Collection, Undated, 2 pages.
Paez, Eduardo; et al. "Generation of a dominant 8-MDa deletion at the left terminus of vaccinia virus DNA," Proc. Natl. Acad. Sci. USA vol. 82, pp. 3365-3369, May 1985. 5 pages.
Qin, Li; et al. "Evolution of and Evolutionary Relationships between Extant Vaccinia Virus Strains," Department of Medical Microbiology & Immunology and Li Ka Shing Institute of Virology, Faculty of Medicine & Dentistry, University of Alberta, Edmonton, AB, Canada. vol. 89, No. 3, Feb. 2015. 16 pages.
Certificate of deposit to CM-CNRG, a Budapest Treaty compliant repository, with accession No. CM-CNRGTB167. 1 page.

*Primary Examiner* — Nicole Kinsey White
(74) *Attorney, Agent, or Firm* — Fish IP Law, LLP

(57) ABSTRACT

A novel attenuated vaccinia virus GAB-1 and its use in treatment of papillomavirus lesions. In preferred embodiments, the Lederle-Chorioallantoic strain of vaccinia virus is serially passaged in chicken embryo-fibroblast (CEF) cells by at least 100 passages. Surprisingly, GAB-1 is highly immunogenic after serial passaging, while being less virulent and safe to use without side effects. Experimentation has found that GAB-1 is much more immunogenic than other strains of vaccinia virus, including Western Reserve (WR) and modified Vaccinia Ankara (MVA). GAB-1 can be used safely in humans for treating tumorous lesions caused by human papillomavirus (HPV).

8 Claims, 11 Drawing Sheets

CEF CELLS INFECTED WITH MVA E2 OR GAB-1 VIRUS

Fig. 5

Table I. Clinical and Pathological Findings in GAB-1 Vaccinated Monkeys Challenged with WR Virus

| Monkey | Vaccine | Antibodies anti-GAB-1 | Clinical Status |
|---|---|---|---|
| 1 | GAB-1 | Positive | Healthy |
| 2 | PBS | Negative | Cramps, weight loss, sever red lesions in extremeties, fewer viremia |
| 3 | GAB-1 | Positive | Healthy |
| 4 | GAB-1 | Positive | Healthy |
| 5 | GAB-1 | Positive | Healthy |

*Fig. 6*

Table II. Summary of Reciprocal antibody titers to Vaccinia virus GAB-1 or WR in Monkeys Immunized with Vaccinia virus GAB-1

| Antibody assay | Week* | Animal Number | | | | |
|---|---|---|---|---|---|---|
| | | 1 | 2 | 3 | 4 | 5 |
| | | Antibody Titer | | | | |
| GAB-1 ELISA | 0 | 50 | 50 | 50 | 50 | 50 |
| | 4 | 500 | 50 | 500 | 500 | 100 |
| WR ELISA | 0 | 50 | 50 | 50 | 50 | 50 |
| | 4 | 1000 | 50 | 1000 | 1000 | 200 |
| Vaccinia WR Neutralizing antibody | 4 | 1000 | 25 | 1000 | 1000 | 1000 |

* Week 0 designated as the time of vaccination. Sera titres were determined at 0 and 4 weeks after immunization.

*Fig. 7*

Table III. Reciprocal antibody titers against Vaccinia virus after vaccination with GAB-1 or MVA E2 in patients presenting precancerous lesions

| Virus Vaccine | Week | Patient number | | | | | | | | | |
|---|---|---|---|---|---|---|---|---|---|---|---|
| | | 1 | 2 | 3 | 4 | 5 | 6 | 7 | 8 | 9 | 10 |
| | | ANTIBODY TITER | | | | | | | | | |
| GAB-1 | 0 | 25 | 50 | 50 | 25 | 50 | - | - | - | - | - |
| | 8 | 2000 | 4000 | 2000 | 2000 | 4000 | - | - | - | - | - |
| MVA E2 | 0 | - | - | - | - | - | 50 | 50 | 50 | 25 | 50 |
| | 8 | - | - | - | - | - | 1000 | 500 | 1600 | 1600 | 500 |

Fig. 8

THERAPEUTIC VACCINE FOR THE TREATMENT OF PAPILLOMAVIRUS LESIONS

FIELD OF THE INVENTION

The field of the invention is attenuated viral vaccine.

BACKGROUND

The following description includes information that may be useful in understanding the present invention. It is not an admission that any of the information provided herein is prior art or relevant to the presently claimed invention, or that any publication specifically or implicitly referenced is prior art.

Human papillomavirus (HPV) is a group of viruses that spread through sexual contact. Some types of HPVs (e.g., HPV-6 and -11) cause genital warts that rarely turn into cancer, while other types (e.g., HPV-16, -18, -31, and -45) can cause cervical, oral, and anal cancer. Warts and precancerous lesions caused by HPV can be treated by cryosurgery, laser, loop electrosurgical excision procedure (LEEP), or surgery. However, these treatments are invasive, and do not cure the viral infection. Although vaccines are available for certain types of HPV, vaccines do not cure cancer or warts caused by HPV.

U.S. Pat. No. 6,582,693 to the inventor in the current application teaches a recombinant vaccinia virus derived from the modified vaccinia Ankara (MVA) encoding and capable of expressing the E2 gene of Bovine papillomavirus, and the use of the virus in the treatment of lesions caused by papillomavirus. However, the attenuated MVA virus has low yields of virus production. U.S. Pat. No. 10,105,436 to Szalay et al. teaches the use of about a dozen strains of vaccinia virus (e.g., New York City Board of Health, Dryvax, ACAM1000, ACAM2000, Lister, EM63, LIVP, Tian Tan, Copenhagen, Western Reserve, and MVA) to induce an anti-tumor immune response. However, Szalay does not teach a strain of vaccinia virus that is more immunogenic.

Thus, there is still a need for a new attenuated vaccinia virus vector that is safe and more immunogenic.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

SUMMARY OF THE INVENTION

The inventive subject matter provides compositions and methods in which a new, highly attenuated vaccine is derived from the Lederle-Chorioallantoic strain of vaccinia virus by serial passaging. Unexpectedly, the attenuated Lederle-Chorioallantoic strain, while being safe to use (i.e., less virulent), is highly immunogenic. It is contemplated that it can be used in the treatment of infectious diseases (e.g., small pox) and tumorous lesions (e.g., papillomavirus (HPV)).

In some embodiments, the attenuated Lederle-Chorioallantoic strains produce a higher antibody titer than wildtype Western Reserve strain of vaccinia virus in an animal. The wildtype Western Reserve strain of vaccinia virus is the most virulent strain of vaccinia virus in animal models. A widely used wild type Western Reserve strain of vaccinia virus is ATCC VR1354; NCBI Ref. Seq: NC-006998.1. It is neurotropic in mice and more virulent than the Wyeth strain. It is lethal to an animal including human, if $10^7$ or more viral particles are given. In preferred embodiments, the attenuated Lederle-Chorioallantoic strains can generate at least 100 times as many viral particles as the MVA strain. In especially preferred embodiments, the attenuated Lederle-Chorioallantoic strains can generate 1000 times as many viral particles compared with the MVA strain.

In some embodiments, the attenuated Lederle-Chorioallantoic strains produce a higher antibody titer than a Modified Vaccinia virus Ankara (MVA) E2 strain of vaccinia virus in a patient. The MVA E2 strain was found to be highly effective against HPV induced lesions. See U.S. Pat. No. 6,582,693 to Rosales. In preferred embodiments, attenuated Lederle-Chorioallantoic strains can generate at least twice as many antibodies as the MVA strain. In especially preferred embodiments, the attenuated Lederle-Chorioallantoic strains can generate four times viral particles compared with the MVA strain.

The attenuated Lederle-Chorioallantoic strains can stimulate the immune system by inducing the host to generate antibodies and cytotoxic cells capable of eliminating tumour lesions caused by viral infections. The tumour cells are destroyed by apoptosis and/or are recognized by immune cells after local injection. It is contemplated that the attenuated Lederle-Chorioallantoic strains can be used to treat lesions caused by papillomavirus located in the throat, cervix, bladder, lungs, or prostate in individuals infected with oncogenic and non-oncogenic papillomaviruses, as well as different types of tumours that are located visually and internally located by tomography and X-rays.

In preferred embodiments, the attenuated Lederle-Chorioallantoic strain is created by attenuating the original Lederle strain of vaccine virus by serial passages in chicken embryo fibroblasts cells (CEF). It is contemplated that other host cells can be used to serially passage the attenuated Lederle-Chorioallantoic strain, for example, a monkey kidney cell line (VERO), and a monkey epithelial cell line (BSC-1). It further contemplated multiple host cells can be used in combination to serially passage the attenuated Lederle strain of vaccine virus.

After serial passaging, the Lederle virus becomes highly attenuated. The Lederle virus strain can be attenuated by cultured into the CEF cells and passaged over multiple times, for example, 50, 100, 200 times, or more, in order to obtain a highly attenuated and highly immunogenic virus. In some embodiments, the attenuated Lederle strain loses at least 5,000 nucleotides from its genome during serial passaging. In preferred embodiments, the attenuated Lederle strain loses between 8,000 and 12,000 nucleotides from its genome during serial passaging.

GAB-1 is an attenuated Lederle-Chorioallantoic strain of vaccinia virus after being passaged 200 times in CEF. The safety of the GAB-1 virus has been tested in animal models in which no adverse effects were observed. The GAB-1 virus can be used for treatment of HPV-associated lesions, including warts and precancerous and cancerous lesions found on the cervix, penis, anus, and throat, as well as use in other types of cancers (for example, bladder, prostate, melanoma, and lungs). The GAB-1 virus can be used for the treatment of both superficial and internal lesions and can be applied locally. It is shown that the GAB-1 virus can lead to the remission of carcinogenic lesions caused by papillomavirus. In addition, the GAB-1 virus can be used to cause regression of HPV lesions and different types of tumours without the possible presence of integrated viruses.

Experiments in human patients have shown that local injection of GAB-1 causes regression of pre-cancerous lesions. Patients presenting papillomavirus lesions showed a reduction up to complete elimination of lesions after treatment with the GAB-1 virus. These results demonstrate that GAB-1 virus is capable of arresting tumour growth. Moreover, animals immunized with GAB-1 are protected against infection by wild type Western Reserve (WR) vaccinia virus (i.e., no signs of sickness are observed). It is further contemplated that the GAB-1 virus can protect animals against poxvirus infections, for example, smallpox.

The present inventive subject matter also provides a pharmaceutical composition or formulation of the GAB-1 virus in a pharmaceutically acceptable carrier or diluent. In some embodiments, the GAB-1 virus is used to prepare an injectable solution for use in humans. It is contemplated that the pharmaceutical composition can be used to eliminate any type of pre-cancer and cancer lesions generated by papillomavirus. In some embodiments, the pharmaceutical composition can be inoculated directly into tumours or lesions, including superficial lesions, and internal lesions observable to the naked eye or through a tomography study or X-ray analysis. It is contemplated that the composition is used in the treatment of all types of human tumours. In preferred embodiments, the composition is used to cure lesions caused by papillomavirus infections.

In some embodiments, the pharmaceutical composition has an adjuvant that helps create a stronger immune response in the subject. Contemplated adjuvants include amorphous aluminum hydroxyphosphate sulfate (AAHS), aluminum hydroxide, aluminum phosphate, potassium aluminum sulfate (Alum), AS04 (Monophosphoryl lipid A (MPL)+aluminum salt), MF59 (Oil in water emulsion composed of squalene), AS01B (Monophosphoryl lipid A (MPL) and QS-21, a natural compound extracted from the Chilean soapbark tree, combined in a liposomal formulation), CpG 1018 (Cytosine phosphoguanine (CpG), a synthetic form of DNA that mimics bacterial and viral genetic material). In preferred embodiments, the adjuvant is an aluminum salt, for example, aluminum hydroxide, aluminum phosphate, and aluminum potassium sulfate, or any combination thereof.

The inventive subject matter also provides a method of immunization, comprising administering a pharmaceutical composition to a subject. In preferred embodiments, the pharmaceutical composition comprises a Lederle-Chorioallantoic strain of vaccinia virus has been serially passaged in chicken embryo fibroblast cells (CEF) by at least 200 passages. In some embodiments, administering the pharmaceutical composition comprising injecting the pharmaceutical composition having between $10^4$ and $10^6$ viral particles into a subject. In preferred embodiments, no adjuvant is added because vaccinia virus does not need additional adjuvants, as it tends to act as an adjuvant by itself, making it a good vector to make vaccines.

In some embodiments, the subject is at least partially protected from infection by smallpox virus after administration of the pharmaceutical composition. In preferred embodiments, the subject is fully protected from infection by smallpox virus after administration of the pharmaceutical composition. In some embodiments, the subject is at least partially protected from infection by Reserve virus (WR) after administration of the pharmaceutical composition. In preferred embodiments, the subject is fully protected from infection by Reserve virus (WR) after administration of the pharmaceutical composition. In preferred embodiments, the subject does not develop adverse side effects after administration of the pharmaceutical composition. In preferred embodiments, the subject is a human.

The inventive subject matter provides a method of treating cancer, comprising administering a pharmaceutical composition to a subject. In preferred embodiments, the pharmaceutical composition comprises a Lederle-Chorioallantoic strain of vaccinia virus has been serially passaged in chicken embryo fibroblast cells (CEF) by at least 200 passages. In some embodiments, administering the pharmaceutical composition comprising injecting the pharmaceutical composition having between $10^4$ and $10^6$ viral particles into a lesion in the subject. In preferred embodiments, the lesion is caused by human papillomavirus (HPV). To be considered effective, the lesion has at least 80% reduction is size, up to 100% eradication 14 weeks after treatment.

It is contemplated that the lesion is in a cervix, anus, penis, or larynx of the subject. It is contemplated that the pharmaceutical composition stimulates the immune system of an animal organism to generate antibodies directed towards cancerous cells. It is also contemplated that the pharmaceutical composition stimulates the immune system of an animal organism to activate cytotoxic cells to kill tumour cells. The composition can be used in animal organisms, specifically in humans.

Various objects, features, aspects and advantages of the inventive subject matter will become more apparent from the following detailed description of preferred embodiments, along with the accompanying drawing figures in which like numerals represent like components. which are responsible for the regression and elimination of precancerous and cancerous lesions.

BRIEF DESCRIPTION OF THE DRAWINGS

FIG. 1 is the characterization of GAB-1 virus infection in cell culture, compared with wildtype Western Reserve (WR) virus.

FIG. 5 is a chart showing the viral yield of GAB-1 virus compared with MVA E2 recombinant vaccine in CEF cells.

FIG. 6 shows a table (Table I) comparing monkeys immunized with GAB-1 and a control monkey injected with PBS buffer.

FIG. 7 shows a table (Table II) further analyzing the antibody levels in monkeys in Table I.

FIG. 8 shows a table (Table III) comparing antibody levels in patients immunized with GAB-1 or MVA E2.

DETAILED DESCRIPTION

Figure 1A:
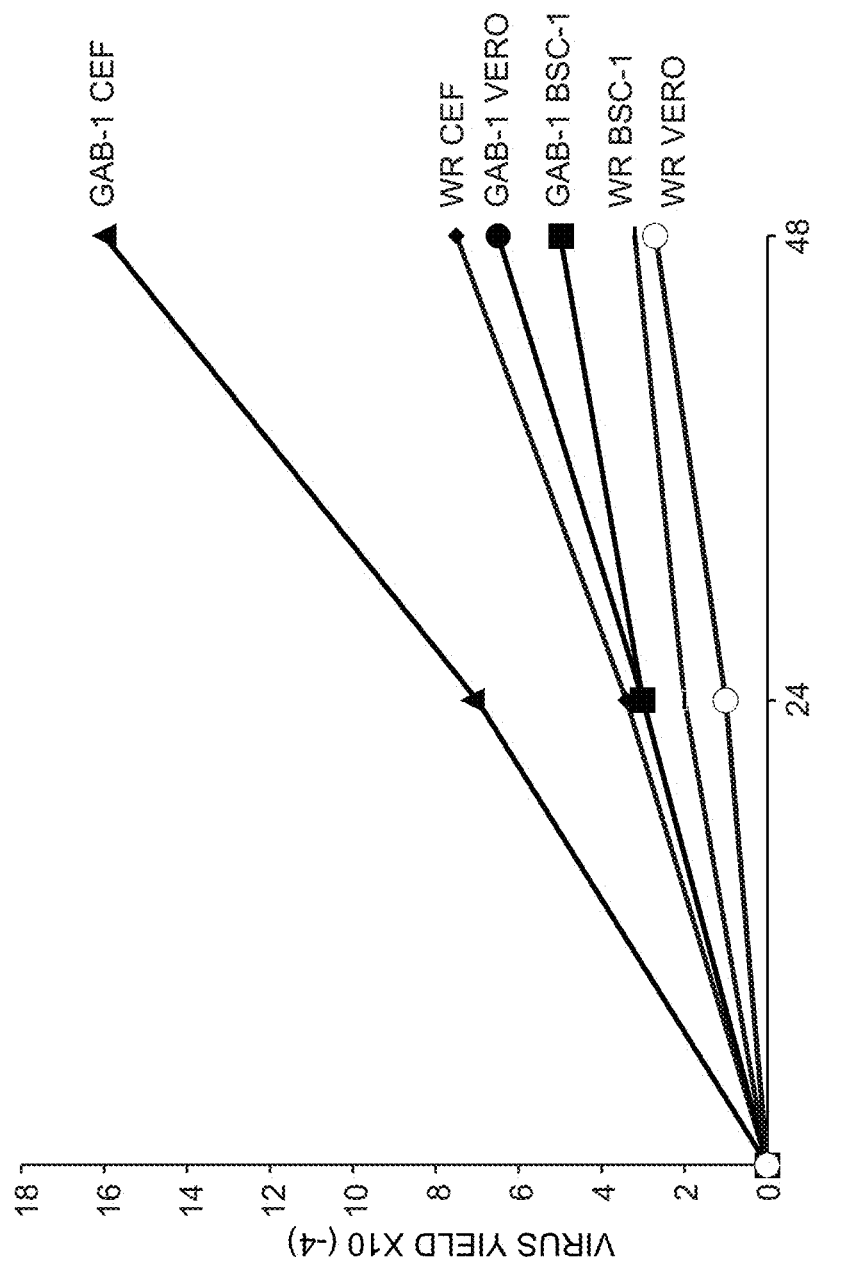
FIG. 1A is a chart of viral yield of GAB-1 and WR viruses in chicken embryo fibroblasts cells (CEF), a monkey kidney cell line (VERO) and a monkey epithelial cell Line BSC-1.

As used in the description herein and throughout the claims that follow, the meaning of "a," "an," and "the"

includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In Table I (as provided in FIG. 6), monkeys 1 and 3-5 are vaccinated with GAB-1, while control monkey 2 is injected with PBS. Monkeys (1 and 3-5) vaccinated with GAB-1 are tested positive for anti-GAB-1 antibody and appear healthy after being challenged with WR virus. The control monkey 2 is tested negative for anti-GAB-1 antibody and appears sick after being challenged with WR virus.

In Table II (as provided in FIG. 7), monkeys 1 and 3-5 showed increased antibody titers against GAB-1 antibody, WR antibody, and vaccinia WR neutralizing antibody, compared to monkey No. 2.

In Table III (as provided in FIG. 8), patients immunized with GAB-1 produces higher antibody titers than patients immunized with MVA E2. This shows that the GAB-1 virus is more immunogenic than MVA E2.

In FIG. 1A, CEF, BSC-1 and VERO cells were infected with GAB-1 or wild type Western Reserve (WR) virus at 0.05 plaque-forming unit (pfu), and harvested at 24 and 48 hours post infection, to measure the multiplication of GAB-1 and WR viruses in CEF, BSC-1 and VERO cells. GAB-1 grows in CEF much more efficiently than in VERO or BSC-1. Surprisingly, GAB-1 grows more efferently than the wild type, unattenuated WR virus, in each cell type.

Figure 1B:
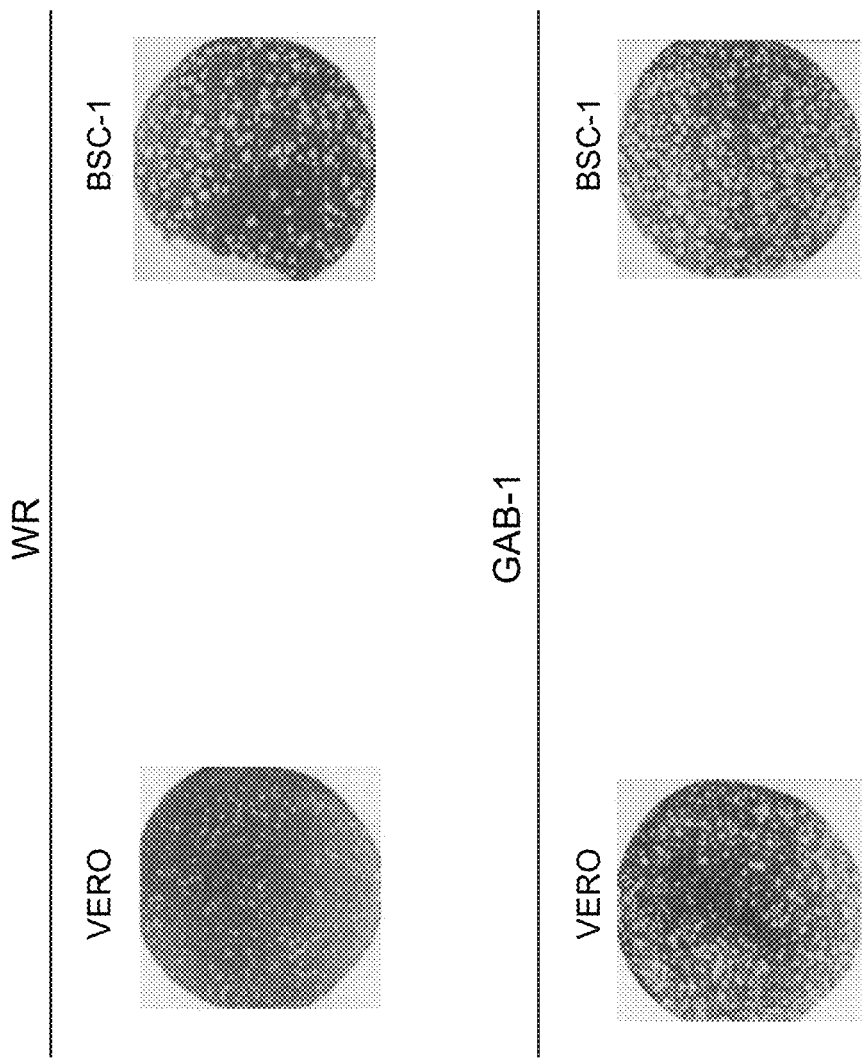
FIG. 1B shows viral plaques of WR and GAB-1 viruses in VERO and BSC-1 cells.

In FIG. 1B, viral yield was analyzed by titrating the different virus preparations in BSC-1 and VERO cells. Plaques were stained with crystal violet at 48 h post infection.

Figure 1C:
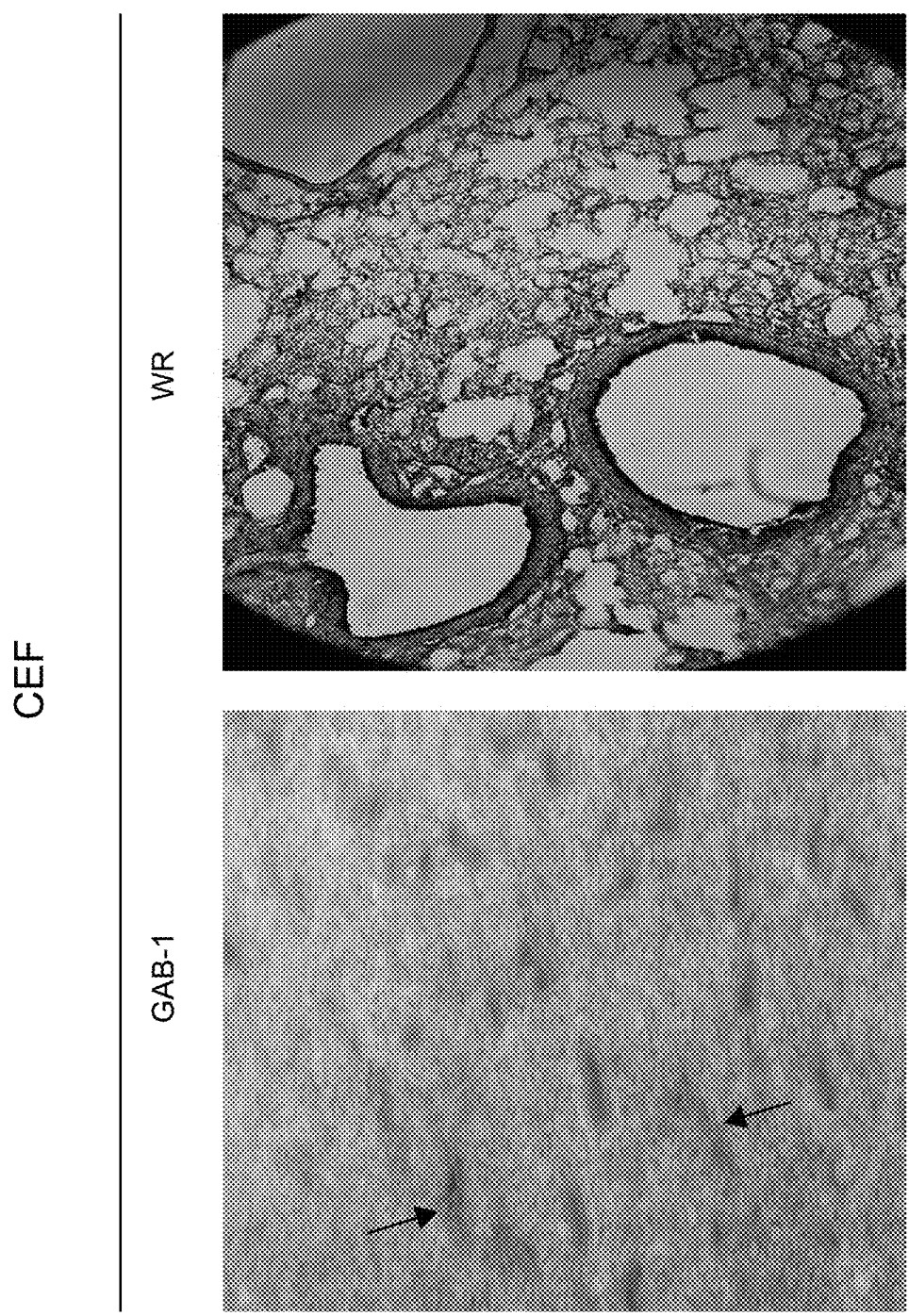
FIG. 1C shows viral plaques of WR or GAB-1 viruses in CEF.

In FIG. 1C, the virulent wildtype WR virus can replicates in CEF and go outside of the cells forming lytic plaques because it is not attenuated. In contrast, the GAB-1 virus is an attenuated virus which does not go outside of the cell (does not form lytic plaques or holes) and can only form morphologic plaques.

Figure 2:
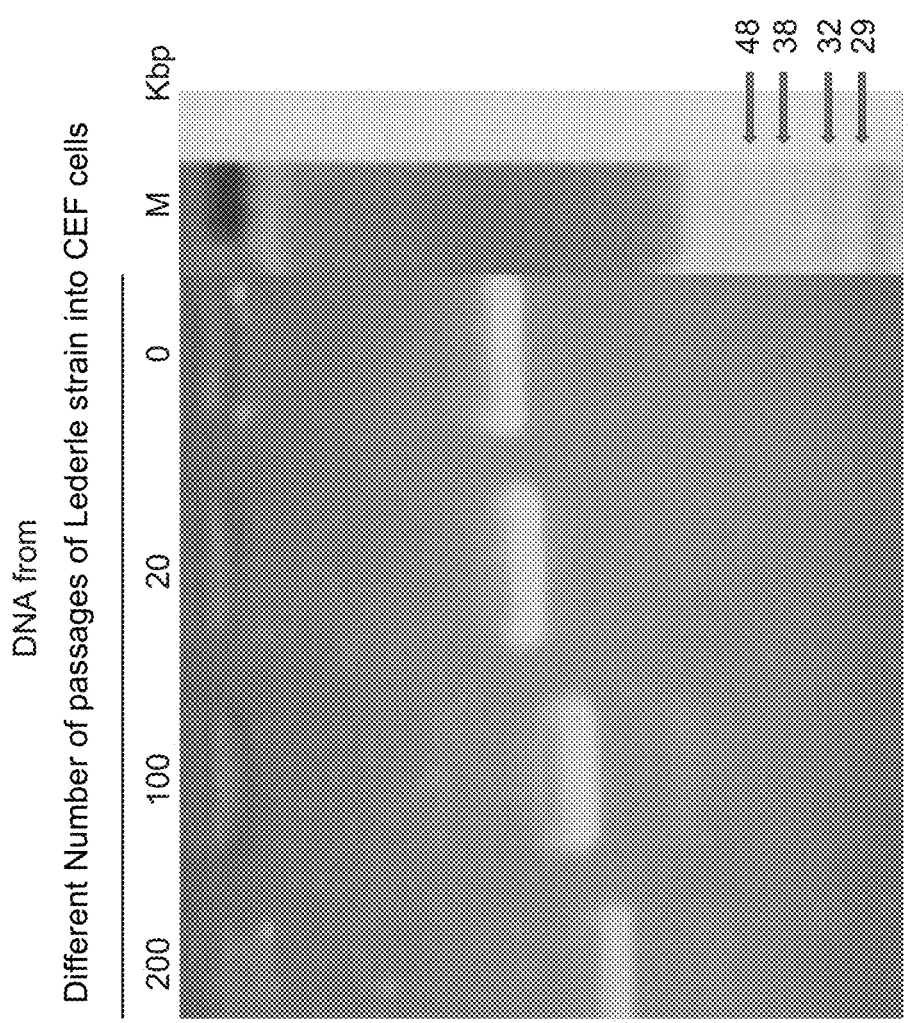
FIG. 2 shows the DNA molecular weight of different isolates from Lederle virus passages over the CEF cells.

In FIG. 2, DNA was extracted from 0, 20, 100 and 200 passages over the CEF cells. The GAB-1 virus lost many nucleotides. GAB-1 cannot grow in most of human cells tested up to now, but can grow very efficiently in CEF cells.

Figure 3A:
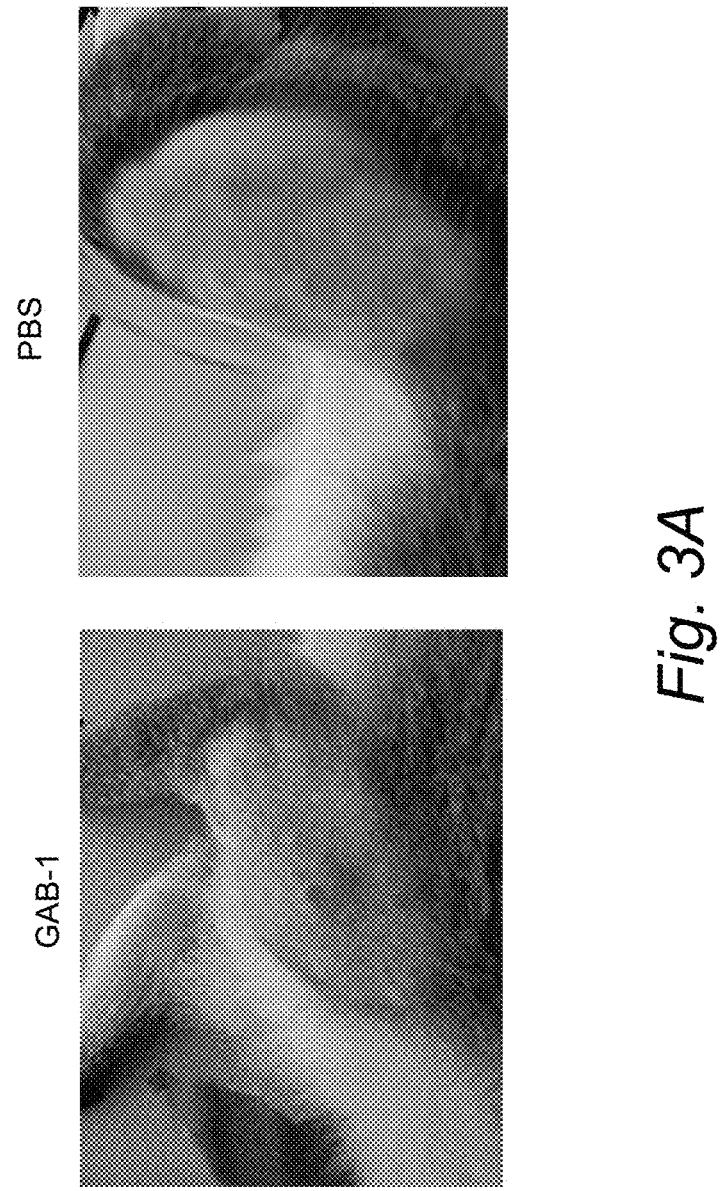
FIG. 3A shows a pustule developed in the upper arm in a monkey 7 days after injection with GAB-1 virus, but not in a monkey injected with PBS.
Figure 3B:
FIG. 3B shows GAB-1 vaccine fully protected monkeys against challenge with the WR virus.
Figure 3B:
Figure 3B:

In FIG. 3A, monkeys were injected with GAB-1 virus vaccine or PBS solution in the upper arm. A pustule developed after 7 days at the site of injection in animals vaccinated with GAB-1, but not in monkey injected with PBS. In FIG. 3B, one month after vaccination, monkeys were challenged with wildtype WR virus. After one week, the control animals were clearly very sick (PBS), while the vaccinated animal (GAB-1) remained healthy.

Figure 4:
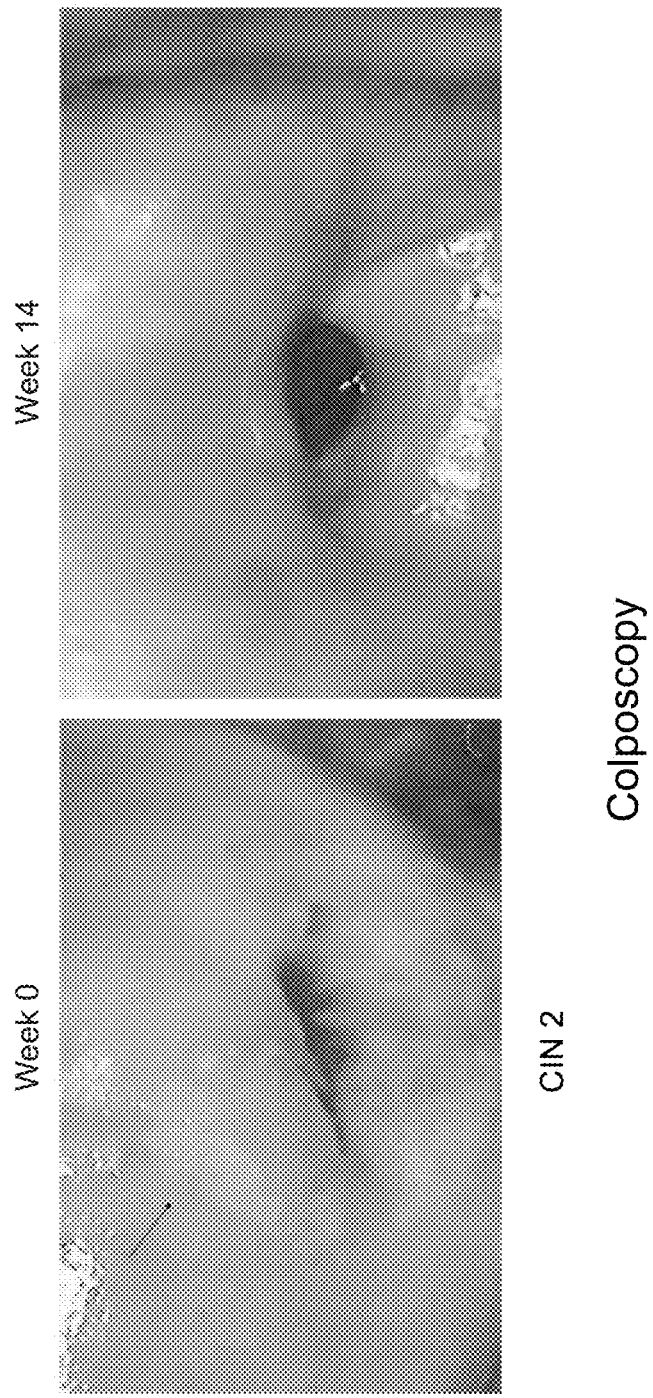
FIG. 4 is a colposcopy showing the disappearance of intraepithelial lesion in patients treated with GAB-1.

In FIG. 4, the aceto-white staining in the uterus reveals papillomavirus infection in a patient, characterized as cervical intraepithelial neoplasia grade 2 (CIN 2). The patient is free of lesions at week 14 after GAB-1 treatment.

Figure 5:
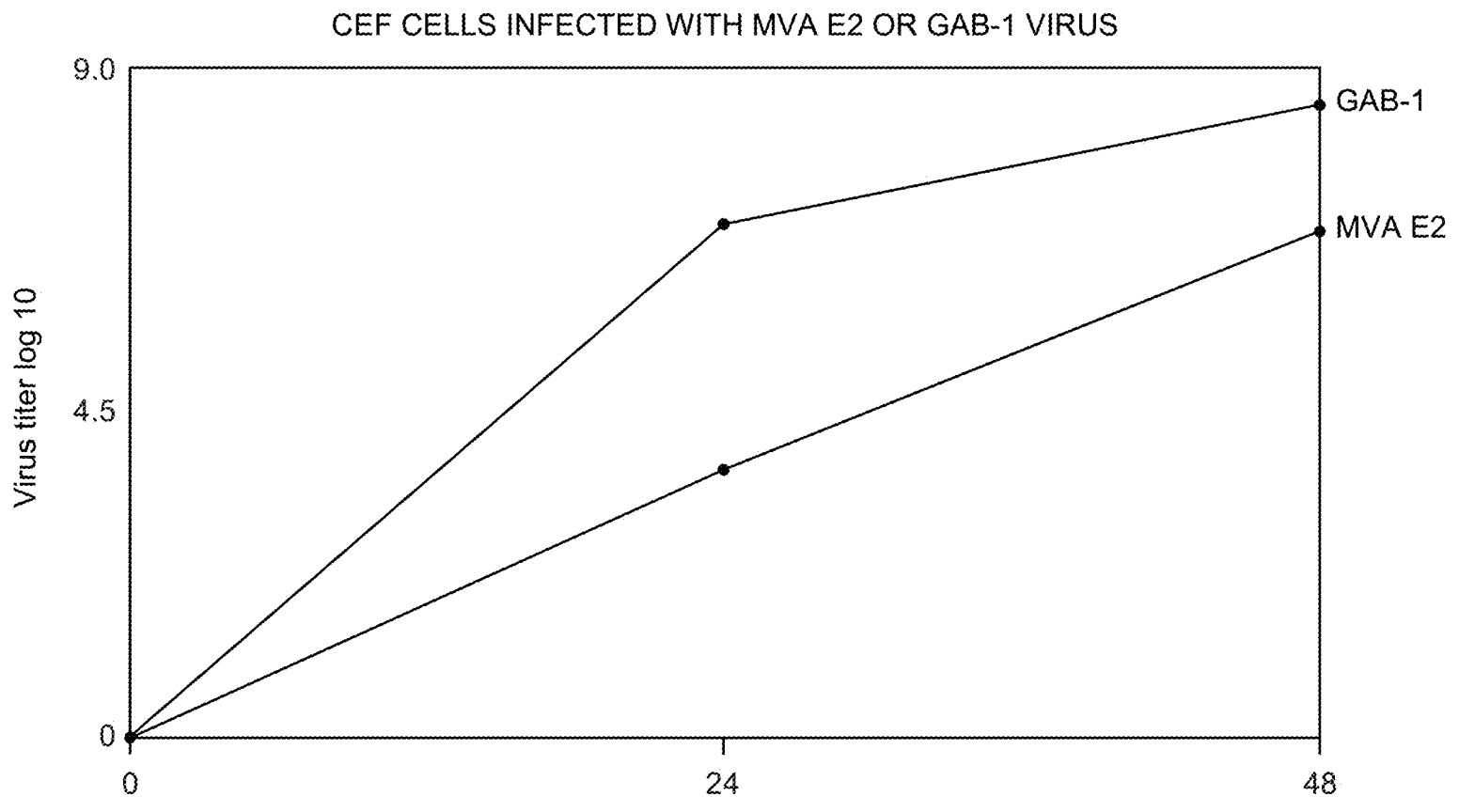

In FIG. 5, CEF cells were infected with GAB-1 or MVA E2 recombinant virus. After 24 and 48 hours viruses were collected and titrated. GAB-1 virus produced more viral particles than did MVA E2 recombinant vaccine. Both GAB-1 and MVA E2 are attenuated and non-virulent.

Example 1

Construction of New Attenuated Vaccinia Virus GAB-1.

Cell and viruses. Monkey-kidney (VERO) and human carcinoma (HeLa) and BSC-1 cells were maintained in a humidified air-5% CO2 atmosphere at 37° C. Chicken embryo fibroblast (CEF) cells were grown in Dulbecco's modified Eagle's medium (DMEM) supplemented with 10% fetal calf serum (Gibco BRL, Gaithersburg, Md.), 20 μM glutamine, and 50 units/ml penicillin, and 50 μg/ml of streptomycin. The vaccinia virus strains Western Reserve (WR) and Lederle-Chorioallantoic were obtained from the American Type Culture Collection (ATCC), Manassas, Va., USA). WR virus was propagated in HeLa cells and the Lederle virus strain was grown in VERO cells. Immediately, BSC-1 cells were infected using the original seed of vaccinia virus (Lederle-Chorioallantoic). After 48 hours of infection 10 different virus plaques were isolated. These virus plaques were grown, first in VERO cells and then in chicken embryo fibroblast cells (CEF). Two virus plaques were selected and about many passages over CEF cells were performed. Two of these virus isolates were used to prepare two different stocks of the new GAB-1 virus.

Once the GAB-1 virus was prepared, we characterized virus replication of GAB-1 in different permissive cell lines.

BSC-1, VERO and CEF cells. These cells were infected with GAB-1 or WR viruses using 0.05 pfu. Virus-infected cells were collected at 24- and 48-hours post-infection. GAB-1 virus produced the double amount of virus as compared with the WR virus in CEF cells (FIG. 1 A). We next analyzed the plaque morphology of the GAB-1 virus by infecting BSC-1 and VERO cells for 48 hours. GAB-1 virus produced smaller plaques as compared with the WR virus (FIG. 1 B). In addition, CEF infected with GAB-1 produced morphologic plaques as compared with the big lytic plaques formed by WR virus (FIG. 1C). This result showed that the GAB-1 virus can replicate efficiently in CEF cells but not in VERO cells (FIG. 1 B and FIG. 1C).

Purification of Recombinant GAB-1 Viruses

Chicken fibroblast cells were grown to a confluence of 85% and then infected with recombinant virus GAB-1 in DMEN medium containing 2.5% horse serum. Infection is induced using 1 virus for every 10 cells. Infection is left for one hour at 37° C. Infected cells are then incubated for 48-72 hours at 37° C., in DMEM medium containing 5% horse serum and in an atmosphere of 4.5% CO2. The infected cells are collected and centrifuged at 2500 rpm for 10 minutes at room temperature.

These collected viruses are resuspended in 20 ml of DMEM-5% with horse serum. They are then frozen and thawed three times in order to completely break the cells and liberate the viruses. Rupture is verified with the assistance of a microscope.

The solution is centrifuged at 2,500 rpm for 10 minutes and the viruses are resuspended in 10 ml of 10 mM Tri HCl, pH: 9 buffer. The viruses are sonicated for 2 minutes and placed in a Dounce homogenizer. The viruses are homogenized with 40 strokes and then centrifuged at 2,500 rpm for 10 minutes. The supernatant containing the viruses is placed in a 37% sucrose bed. It is centrifuged in rotor SW28 at 13,500 rpm, 80 min, 4° C. The viruses located in the bottom of the tube is resuspended in physiological saline solution of PBS, pH:7.4. The viruses are stored in aliquots of 1 ml and kept at −70° C. The number of particles is initially calculated measuring the absorbance of the virus solution at 260 nm. A unit of virus at 260 nm is approximately $1.3 \times 10^{10}$ virus/ml, which is approximately equal to $5 \times 10^{8}$ live viruses. The number of viral particles is also measured with the assistance of a specific antibody against the vaccinia virus, using it in GAB-1-infected cells. In this way live viruses can be counted as compared with infected cells.

Example 2

DNA Analysis of Consecutive Passages of Lederle Strain of Vaccinia Virus Over CEF Cells Viruses from 0, 20, 100 and 200 passages of Lederle virus were grown in CEF cells using Dulbecco modified Eagle medium (DEMEM) (Gibco BRL, Gaithesburg, Md.) supplemented with 10% horse serum (Gibco BRL, Gaithesburg, Md.). Cells were maintained in a humidified air-5% CO2 atmosphere at 37° C. DNA virus from different passages were isolated by phenol-chloroform extraction followed by ethanol precipitation. DNA was quantified by densitometry and analysed by agarose gel 0.4%. (FIG. 2). It was found that by passing the Lederle strain into CEF cells the virus was losing several thousands of nucleotides from its genome. (FIG. 2).

Example 3

Safety of the GAB-1 Vaccinia Virus.

GAB-1 Attenuated Virus Fully Protects Monkeys Against a Lethal Challenge with the WR Virus.

In order to test the safety, efficacy and potency of the GAB-1 virus, four monkeys' captive-bred adult (5-13 years) healthy male monkeys (*Cercopithecus aethiops*) were intradermally immunized with $10^{5}$ pfu of the GAB-1 virus and one monkey injected with physiological solution (PBS). All monkeys were kept and maintained in negatively pressurized P3 facilities following good principles of laboratory animal care. Monkeys were immunized by the multiple-puncture technique using a bifurcated needle as described (Frey et al., 2002). The injections were done by performing 15 strokes directly into the skin of the upper arm. It was observed that in vaccinated animals a small pustule of 0.3 cm of diameter appeared three days after injection. This pustule became red after three days and finally dried by day fourteen and disappear. (FIG. 3A) The vaccination discomfort was very mild at most because monkeys did not present rash, or pain at the place of injection. One month after immunization animals were challenged intramuscularly with $10^{8}$ pfu of WR virus. Half of this virus dose was injected into the triceps muscle, and the other half into the femora's muscle. Animals immunized with GAB-1 showed no evidence sickness, and remained clinically healthy for two months after challenge (FIG. 3 B). These monkeys did not change their food intake during the whole study. In contrast, the non-vaccinated control monkey showed a sick appearance and red spots in the skin after the fourth day of challenge. This animal stopped eating after the fifth day of challenge with an increase of temperature fever. He also presented cramps, weight lost and severe red lesions in extremities, due to virus spreading. In contrast all GAB-1 vaccinated animals remained healthy all the time without the presence adverse side effects. (Table I). In addition, all immunized animals with GAB-1 virus generated antibodies against the virus, showing that GAB-1 virus is a good immunogen. (Table II).

Example 4

Immune response generated in monkeys after GAB-1 immunization. Vaccinia virus antibody responses against GAB-1 and WR were analyzed in animals vaccinated with GAB-1. Briefly, ELISA plates were coated with either $5 \times 10^{5}$ purified virus particles of WR or GAB-1 virus. Sera from animals were collected at the beginning of vaccination and 4 weeks later after immunization. Serum dilutions were added to plates and incubated overnight at 4° C. Plates were then washed three times with phosphate buffer saline (PBS), and incubated with a 1/2000 dilution of horseradish peroxidase-conjugated Protein A (Sigma Aldrich) for 1 hr. Following three more washes, the plates were incubated with the peroxidase substrate 0-phenylene diamine (Sigma Aldrich) at room temperature during 30 min. Absorbance was read at 405 nm on an ELISA plate reader (Bio-Tek Instruments). All monkeys vaccinated with GAB-1 generated antibodies against the virus. In addition, these antibodies also react against the WR virus. In contrast, a monkey (number 2) injected with PBS does not generated antibodies against vaccinia virus. These results showed that the GBA-1 virus can efficiently stimulate the immune system (Table II).

Neutralizing Antibody Responses in Monkeys after Immunization with the GAB-1 Virus.

Because the WR virus has a very similar genome-sequence to the variola virus (smallpox) and because the GAB-1 vaccination protected animals against challenge with WR virus. We decided to analyze the capacity of the antibodies generated in immunized animals with GAB-1 virus to neutralize the WR virus in infection experiments. Serial dilutions of sera from GAB-1 vaccinated monkeys were mixed with WR virus and immediately added to BSC-1 cells to allow viral infection. Infectious viruses were detected by counting the number of plaques formed. Sera from the four vaccinated animals can neutralize the WR virus (Table II). In contrast, antibodies from the un-vaccinated animal did not neutralize the WR virus. Sera neutralizing titers were approximately 1/1000 in all animals. These results showed that antibodies against the GAB-1 virus efficiently bind the WR virus and can prevent viral infection. Taken together, these results show GAB-1 virus is a safe and efficient virus to stimulate the immune system.

Example 5

Study Design and Subjects.

Clinical Protocol for Testing the Potential of the GAB-1 Virus in the Treatment of Papillomavirus Lesions.

A phase I, II and III clinical protocol was conducted in which approximately 200 patients (male and female) with HPV intraepithelial lesions were treated with GAB-1 virus. Patients were recruited from the following medical institutions in Mexico: Hospital de Cuautitlan, in Estado de Mexico; Hospital de la mujer, in Michoacan state; Sanatorio San Francisco, Hospital General de Veracruz, Hospital 20 de Noviembre, ISSTE, Hospital Militar, and Hospital de Nutricion, Instituto Nacional de Cancerologia, in Veracruz state; and in Venezuela: Inversiones Milfred Medical. Patients were admitted to the protocol once the relevant eligibility criteria had been met. These criteria included presence of papillomavirus (HPV), age between 14 and 60 years, not to be pregnant and have CIN 1, CIN 2, CIN 3 or condyloma lesions, including several clinical laboratory exams, a complete physical exam, and the clinical history of the patient. The protocol has been approved by the Ethics and scientific committee from the hospitals. Before starting the treatment with GAB-1, the physician revised all these data and confirmed that the patient was eligible for the protocol. We used $10^5$ GAB-1 viral particles for each dose of the viral vaccine. The GAB-1 virus was injected directly into the uterus in a radial clock-wise fashion at 3, 6, 9, and 12 o'clock once a week during six weeks for women; or directly into the urethra once a week during five weeks, for men. In cases when lesions were visible, for example in vulva and anus, GAB-1 was also applied locally at the base of each lesion. (FIG. 4).

We also analyzed the difference in immunogenicity between our previous MVA E2 recombinant virus vaccine and the present GAB-1 virus vaccine. We found that by using 100-fold less of the GAB-1 virus vaccine ($10^5$ viral particles) compared with the $10^7$ viral particles of the MVA E2 that we been using in the past 20 years. W were able to eliminate all the papilloma lesions present in the patients. These results show that the GAB-1 virus can stimulate very efficiently the immune system, and is capable of completely eliminate all papillomavirus lesions in patients by using much less virus as we did for the MVA E2 virus vaccine.

In addition, we compared the humoral immune response generated against the GAB-1 or the MVA E2 recombinant vaccine (Table III). We observed that patients vaccinated with GAB-1 virus produced more antibodies anti-vaccine than the MVA E2 recombinant virus. Surprisingly, GAB-1 virus is much more immunogenic than the MVA E2 virus that has been used to produce many vaccines for several virus infectious diseases.

Comparative Virus Production Between GAB-1 Virus and MVA E2 Recombinant Virus.

Chicken embryo fibroblast (CEF) were obtained from 11-day fertile eggs. Briefly, chicken body was minced and cells were obtained by addition of 0.25% trypsin. Cells were harvested by centrifugation and resuspended in Dulbecco's modified Eagle's medium (DMEM) supplemented with 10% horse serum (Gibco, BRL), 20 uM glutamine, 50 unit/ml penicillin and 50 ug of streptomycin in a humidified air-5% $CO_2$ atmosphere at 370 C. After cells were collected and attached to microcarriers (Cytodex) and grown is a 15-liter Bioreactor Celligen-Plus. Cells were infected either with GAB-1 or MVA E2 recombinant virus. The viruses were collected at 24 and 48 hours after infection. Immediately the infected-cells were freeze-thawed three times. Viruses were purified by two successive sucrose (40-10%) zonal centrifugation steps. The purified viruses were titrated on CEF and stored at −70° C.

Surprisingly, there was a big difference in virus yield production between GAB-1 and MVA E2 recombinant virus. (FIG. 5). Under the same conditions we obtained almost 50-100 times more GAB-1 virus than the MVA E2 recombinant virus. This stronger viral yield is a great advantage for virus vaccine production for commercial purposes.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

Definitions

Gene: Refers to a sequence of DNA that carries the information for synthesis of a polypeptide or protein.

Infection: Refers to the penetration of an infectious agent into a cell, and if the conditions are sufficient, the microorganism can be replicated within the cell.

Expression systems: Systems in which foreign proteins can be synthesized within bacteria or cells.

Through cloning of genes into expression vectors, it is possible by means of transfection techniques to introduce genes into cells and bacteria and for these genes to be efficiently expressed. These vectors can be plasmids or recombinant viruses normally introduced into bacteria, insect cells, yeast cells, or animal cells.

For example, if the protein is expressed in a bacterial system, a high quantity can be produced. However, there is a drawback: if the protein is unstable, it may rapidly degrade, and the yield would be very low. Another disadvantage is that if eukaryotic genes are expressed in the bacterium, and the protein requires post-translational modifications (glycosylations for example), then a non-functional protein is synthesized. Expressing these genes in systems such as yeasts or eukaryotic cells solves the problem.

Yeast systems are very efficient, since these cells grow at room temperature and do not require expenditure of energy to raise their temperature. But as with bacteria, they do not have all the post-translational modification systems, which means that they also have limitations.

Viral expression systems such as baculovirus (a virus that infects insect cells) are used a great deal today, since they can express genes efficiently and have the advantage that they can excrete the protein into the external environment, facilitating its purification. However, as there are only two or three glycosylation systems, not all proteins expressed in this system are functional.

Viral vectors such as poxvirus can be excellent expression vectors. For example, the vaccinia virus belonging to this family has been used for the expression of many biologically interesting proteins, and since it is expressed in mammalian cells, the proteins maintain their normal biological activity.

An even more innovative step is the use of the vaccinia virus to express exogenous proteins that in turn serve as immunogenic agent for use as vaccinations against some diseases or infectious agent in particular. Also, the use of these vectors is safe, since they do not cause adverse effects on people or animals that are vaccinated. This has already been described and demonstrated with a great number of vaccines used to fight diseases such as prostate cancer; hepatitis A, B, and C; rabies, HIV, mumps, flu, parainfluenza, malaria, tuberculosis, or against *Plasmodium*, hantaan virus, SARS, and breast cancer. In all cases the vaccine's efficacy has been validated through experiments with laboratory animals.

Samples of GAB-1 virus have been placed on deposit under the terms of the Budapest Agreement at Collecion de Microorganismos del CNRG (Boulevard de la Biodiversidad No. 400, Col Rancho las Cruces CP. 47600, Tepatitlan de Morelos, Jalisco, Mexico) as GAB-1 VIRUS DE LA VACCINIA ATENUADO and under Accession No. CM-CNRG TB167. The deposit was made on Sep. 22, 2020.

REFERENCES

1. Hochstein-Mintzel V, Hanichen T, Huber H C, et al. [An attenuated strain of vaccinia virus (MVA). Successful intramuscular immunization against vaccinia and variola (author's transl)]. Zentralbl Bakteriol Orig A 1975; 230: 283-297.
2. Mayr A, Stickl H, Muller H K, et al. [The smallpox vaccination strain MVA: marker, genetic structure, experience gained with the parenteral vaccination and behavior in organisms with a debilitated defence mechanism (author's transl)]. Zentralbl Bakteriol B 1978; 167:375-390.
3. Stickl H. [The present-day situation in smallpox vaccination]. Med Klin 1975; 70:1893-1898.
4. Antoine G, Scheiflinger F, Dorner F, et al. The complete genomic sequence of the modified vaccinia Ankara strain: comparison with other orthopoxviruses. Virology 1998; 244:365-396.
5. Meyer H, Sutter G, Mayr A. Mapping of deletions in the genome of the highly attenuated vaccinia virus MVA and their influence on virulence. J Gen Virol 1991; 72 (Pt 5):1031-1038.
6. Stickl H, Hochstein-Mintzel V, Mayr A, et al. [MVA vaccination against smallpox: clinical tests with an attenuated live vaccinia virus strain (MVA) (author's transl)]. Dtsch Med Wochenschr 1974; 99:2386-2392.
7. Lathe R, Kieny M P, Gerlinger P, et al. Tumour prevention and rejection with recombinant vaccinia. Nature 1987; 326:878-880.
8. Sutter G, Wyatt L S, Foley P L, et al. A recombinant vector derived from the host range-restricted and highly attenuated MVA strain of vaccinia virus stimulates protective immunity in mice to influenza virus. Vaccine 1994; 12:1032-1040.
9. Albarran Y C A, de la Garza A, Cruz Quiroz B J, et al. MVA E2 recombinant vaccine in the treatment of human papillomavirus infection in men presenting intraurethral flat condyloma: a phase I/II study. BioDrugs 2007; 21:47-59.
10. Cabo Beltran O R, Rosales Ledezma R. MVA E2 therapeutic vaccine for marked reduction in likelihood of recurrence of respiratory papillomatosis. Head Neck 2019; 41:657-665.
11. Corona Gutierrez C M, Tinoco A, Navarro T, et al. Therapeutic vaccination with MVA E2 can eliminate precancerous lesions (CIN 1, CIN 2, and CIN 3) associated with infection by oncogenic human papillomavirus. Hum Gene Ther 2004; 15:421-431.
12. Garcia-Hernandez E, Gonzalez-Sanchez J L, Andrade-Manzano A, et al. Regression of papilloma high-grade lesions (CIN 2 and CIN 3) is stimulated by therapeutic vaccination with MVA E2 recombinant vaccine. Cancer Gene Ther 2006; 13:592-597.
13. Rosales C, Graham V V, Rosas G A, et al. A recombinant vaccinia virus containing the papilloma E2 protein promotes tumor regression by stimulating macrophage antibody-dependent cytotoxicity. Cancer Immunol Immunother 2000; 49:347-360.
14. Rosales R, Lopez-Contreras M, Rosales C, et al. Regression of human papillomavirus intraepithelial lesions is induced by MVA E2 therapeutic vaccine. Hum Gene Ther 2014; 25:1035-1049.
15. Valdez Graham V, Sutter G, Jose M V, et al. Human tumor growth is inhibited by a vaccinia virus carrying the E2 gene of bovine papillomavirus. Cancer 2000; 88:1650-1662.
16. de Sanjose S, Diaz M, Castellsague X, et al. Worldwide prevalence and genotype distribution of cervical human papillomavirus DNA in women with normal cytology: a meta-analysis. Lancet Infect Dis 2007; 7:453-459.
17. Ghosh P, Ghosh D D, Majumdar Giri A, et al. Polymerase chain reaction and deoxyribonucleic acid-sequencing based study on distribution of human papillomavirus 16/18 among histopathological types of cervical intra-epithelial neoplasia and primary invasive cervical carcinoma: A scenario in North Bengal, India. J Midlife Health 2014; 5:14-22.
18. Hossein R, Behzad S, Tahar M, et al. Prevalence of human papillomavirus genotypes associated with cervical and breast cancers in iran. Monoclon Antib Immunodiagn Immunother 2013; 32:399-403.
19. Powell N, Cuschieri K, Cubie H, et al. Cervical cancers associated with human papillomavirus types 16, 18 and 45 are diagnosed in younger women than cancers associated with other types: a cross-sectional observational study in Wales and Scotland (UK). J Clin Virol 2013; 58:571-574.
20. Stanley M A. Prognostic factors and new therapeutic approaches to cervical cancer. Virus Res 2002; 89:241-248.
21. Best S R, Niparko K J, Pai S I. Biology of human papillomavirus infection and immune therapy for HPV-related head and neck cancers. Otolaryngol Clin North Am 2012; 45:807-822.
22. Gissmann L, Diehl V, Schultz-Coulon H J, et al. Molecular cloning and characterization of human papilloma virus DNA derived from a laryngeal papilloma. J Virol 1982; 44:393-400.

23. Heck J E, Berthiller J, Vaccarella S, et al. Sexual behaviours and the risk of head and neck cancers: a pooled analysis in the International Head and Neck Cancer Epidemiology (INHANCE) consortium. Int J Epidemiol 2010; 39:166-181.
24. Goon P, Sonnex C, Jani P, et al. Recurrent respiratory papillomatosis: an overview of current thinking and treatment. Eur Arch Otorhinolaryngol 2008; 265:147-151.
25. Venkatesan N N, Pine H S, Underbrink M P. Recurrent respiratory papillomatosis. Otolaryngol Clin North Am 2012; 45:671-694, viii-ix.
26. Rosales R, Sutter G, Moss B. A cellular factor is required for transcription of vaccinia viral intermediate-stage genes. Proc Natl Acad Sci USA 1994; 91:3794-3798.
27. Sutter G, Ramsey-Ewing A, Rosales R, et al. Stable expression of the vaccinia virus K1L gene in rabbit cells complements the host range defect of a vaccinia virus mutant. J Virol 1994; 68:4109-4116.
28. Liu R, Mendez-Rios J D, Peng C, et al. SPI-1 is a missing host-range factor required for replication of the attenuated modified vaccinia Ankara (MVA) vaccine vector in human cells. *PLoS Pathog* 2019; 15:e1007710.
29. Alazawi W, Pett M, Arch B, et al. Changes in cervical keratinocyte gene expression associated with integration of human papillomavirus 16. Cancer Res 2002; 62:6959-6965.
30. Lang Kuhs K A, Porras C, Schiller J T, et al. Effect of different human papillomavirus serological and DNA criteria on vaccine efficacy estimates. Am J Epidemiol 2014; 180:599-607.
31. Rosales-Rueda M F. Family investment responses to childhood health conditions: intrafamily allocation of resources. J Health Econ 2014; 37:41-57.
32. Prazsák I, Tombácz D, Szücs A, Dénes B, Snyder M, Boldogkői Z. 2018. Full genome sequence of the Western Reserve strain of vaccinia virus determined by third-generation sequencing. Genome Announc 6:e01570-17. https://doi.org/10.1128/genomeA.01570-17.
33. Zeh H J, Downs-Canner S, McCart J A, Guo Z S, Rao U N M, Ramalingam L, Thorne S H, Jones H L, Kalinski P, Wieckowski E, O'Malley M E, Daneshmand M, Hu K, Bell J C, Hwang T H, Moon A, Breitbach C J, Kim D H, Bartlett D L. 2015. First-in-man study of Western Reserve strain oncolytic vaccinia virus: safety, systemic spread, and antitumor activity. Mol Ther 23:202-214. doi: 10.1038/mt.2014.194.
34. D. Huw Davies, Linda S. Wyatt et al, Antibody Profiling by Proteome Microarray Reveals the Immunogenicity of the Attenuated Smallpox Vaccine Modified Vaccinia Virus Ankara Is Comparable to That of Dryvax. J Virol. 2008 January; 82(2):652-63. Epub 2007 Oct. 31.
35. Viviana Valadez Graham, Gerd Sutter, et al. Human tumor growth is inhibited by a vaccinia virus carrying the E2 gene of bovine papillomavirus. Cancer. 2000 Apr. 1; 88(7):1650.

What is claimed is:

1. A method of treating a cancer in an individual, comprising:
administering a therapeutically effective amount of a pharmaceutical composition comprising the attenuated Lederle-Chorioallantoic GAB-1 strain of vaccinia virus to the individual, wherein the cancer is caused by human papillomavirus.

2. The method in claim 1, wherein the pharmaceutical composition comprises between $10^4$ and $10^6$ viral particles of the attenuated Lederle-Chorioallantoic GAB-1 strain of vaccinia virus.

3. The method in claim 1, wherein the cancer is cervical intraepithelial neoplasia and wherein the therapeutically effective amount of attenuated Lederle-Chorioallantoic GAB-1 strain of vaccinia virus is selected to reduce size of cervical intraepithelial neoplasia by at least 80%.

4. The method of claim 1, further comprising administration of an adjuvant to the individual.

5. A method of treating a lesion caused by human papilloma virus (HPV) in an individual, comprising:
administering a therapeutically effective amount of a pharmaceutical composition comprising the attenuated Lederle-Chorioallantoic GAB-1 strain of vaccinia virus to the individual.

6. The method of claim 5, wherein the lesion is a wart.

7. The method of claim 5, wherein the lesion is a pre-cancerous lesion.

8. The method of claim 5, further comprising administration of an adjuvant to the individual.

* * * * *